(12) United States Patent
Horiuchi et al.

(10) Patent No.: US 7,502,439 B2
(45) Date of Patent: Mar. 10, 2009

(54) RADIOGRAPHIC APPARATUS AND METHOD OF USING THE SAME

(75) Inventors: Tetsuya Horiuchi, Tokyo (JP); Junko Sekiguchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/474,764

(22) Filed: Jun. 26, 2006

(65) Prior Publication Data

US 2006/0291614 A1  Dec. 28, 2006

(30) Foreign Application Priority Data

Jun. 28, 2005  (JP) .............................. 2005-188253

(51) Int. Cl.
*G21K 1/12* (2006.01)
(52) U.S. Cl. ............................................ 378/16; 378/4
(58) Field of Classification Search .................... 378/8, 378/16, 4, 5, 20
See application file for complete search history.

(56) References Cited

U.S. PATENT DOCUMENTS

| 5,379,333 | A | | 1/1995 | Toth |
|---|---|---|---|---|
| 5,450,462 | A | | 9/1995 | Toth et al. |
| 5,668,845 | A | * | 9/1997 | Migita ............................. 378/4 |
| 7,088,798 | B2 | * | 8/2006 | Chen et al. ...................... 378/4 |
| 2002/0080918 | A1 | * | 6/2002 | Sako ........................... 378/115 |
| 2003/0156765 | A1 | * | 8/2003 | Yamamichi ................. 382/305 |
| 2004/0131141 | A1 | * | 7/2004 | Horiuchi ......................... 378/4 |
| 2005/0041772 | A1 | * | 2/2005 | Nishide ......................... 378/19 |
| 2005/0053190 | A1 | * | 3/2005 | Gohno ......................... 378/16 |
| 2006/0018435 | A1 | | 1/2006 | Toth et al. |

FOREIGN PATENT DOCUMENTS

JP  2005-058651  3/2005

* cited by examiner

*Primary Examiner*—Hoon Song
(74) *Attorney, Agent, or Firm*—Armstrong Teasdale LLP

(57) ABSTRACT

To enable radiation rays to be efficiently used. A scout scan parameter setting unit sets a rotation movement position to which an X-ray tube and an X-ray detector are moved so as to rotate around a subject on the basis of subject information of a subject on which a scout scan is performed at the time of performing a scout scan. At the time of starting execution of the scout scan, a rotating unit moves the X-ray tube and the X-ray detector so as to rotate around the subject to the rotation movement position which is set by the scout scan parameter setting unit. After that, a scout scan is performed in the rotation movement position.

19 Claims, 8 Drawing Sheets

FIG. 6

| Sex | Region | Age | Body posture | Rotation movement position (view angle "v") |
|---|---|---|---|---|
| Female | Chest region | 0 to 40 | Face-up position | 180° |
| Female | Chest region | 0 to 40 | Face-down position | 0° |
| Female/Male | Neck region | - | Face-up position | 180° |
| Female/Male | Neck region | - | Face-down position | 0° |
| Female/Male | Neck region | - | Face-up position | 180° |
| Female/Male | Neck region | - | Face-down position | 0° |
| ... | ... | ... | ... | ... |
| ... | ... | ... | ... | ... |

FIG. 7

| Sex | Region | Body posture | Rotation movement position (view angle "v") | Organ dose position for the mammary gland |
|---|---|---|---|---|
| Female | Chest region | Face-up position | 180° | 1.2mGy |
| Female | Chest region | Face-up position | 0° | 7.5mGy |
| Female | Chest region | Face-down position | 0° | 7.5mGy |
| Female | Chest region | Face-down position | 180° | 1.2mGy |
| ... | ... | ... | ... | ... |
| ... | ... | ... | ... | ... |

RADIOGRAPHIC APPARATUS AND METHOD OF USING THE SAME

CROSS REFERENCE TO RELATED APPLICATIONS

This application claims the benefit of Japanese Application No. 2005-188253 filed Jun. 28, 2005.

BACKGROUND OF THE INVENTION

The present invention relates to a radiographic apparatus and, more particularly, to a radiographic apparatus for generating a scout image of a subject by performing, in a rotation movement position to which an irradiator for applying radiation rays and a detector for detecting the radiation rays which have passed the subject are moved so as to rotate around the subject, a scout scan in which the irradiator irradiates the subject with radiation rays, and the radiation rays passed through the subject are detected by the detector.

A radiographic apparatus such as an X-ray CT (Computed Tomography) apparatus generates a slice image of a section of a subject on the basis of projection data obtained by scanning the subject with radiation rays such as X-rays. Such a radiographic apparatus is used in wide-range applications such as medical and industrial applications.

An X-ray CT apparatus performs a scout scan for generating a scout image in order to set scan parameters prior to execution of a scan for generating a slice image.

In the scout scan, an X-ray tube for emitting an X-ray to a subject and an X-ray detector for detecting the X-ray applied from the X-ray tube and passed through the subject are fixed in positions forming a predetermined view angle around the subject. In the fixed position at the predetermined view angle, an X-ray is applied from the X-ray tube to the subject, and the X-ray passed through the subject is detected by the X-ray detector. On the basis of projection data generated by the X-ray detector which has detected the X-ray, a scout image as a radioscopic image of the subject is generated and displayed.

After that, the operator refers to the scout image generated by the scout scan and enters scan parameters such as a slice position corresponding to a section whose slice image is generated. A scan such as an axial scan or a helical scan is performed to generate a slice image of the section in the slice position entered by the operator (refer to, for example, Japanese Patent Laid-Open No. 2005-58651).

The scout scan is performed by fixing, for example, the X-ray tube in front of a chest region of the subject supported in a face-up position on a table and emitting an X-ray from the position.

Consequently, when the subject is a female and a scout scan is performed so as to include a chest region, in some cases, the dose of radiation on the mammary gland having high radiation sensitivity is large and it is difficult to acquire images by effectively using radiation rays such as X-rays. Also in the case of a region having high radiation sensitivity such as a lens in the head of a subject or thyroid in the neck in/around the body surface of the subject, there is a similar inconvenience.

An object of the present invention is, therefore, to provide a radiographic apparatus capable of easily capturing an image by efficiently utilizing radiation rays.

SUMMARY OF THE INVENTION

To achieve the object, a radiographic apparatus of the present invention includes: an irradiator for irradiating a subject with radiation rays; a detector for detecting the radiation rays applied from the irradiator and passed through the subject; a rotating unit for moving the irradiator and the detector so as to rotate around the subject to a rotation movement position for performing the scout scan; an input unit in which subject information of the subject on which the scout scan is performed is entered; and a setting unit for setting the rotation movement position in which the scout scan is performed on the basis of the subject information entered in the input unit.

According to the present invention, a radiographic apparatus capable of easily acquiring an image by efficiently utilizing radiation rays can be provided.

BRIEF DESCRIPTION OF THE DRAWINGS

FIG. 6 is a diagram showing rotation movement information stored in a storing device 61 in the embodiment according to the invention.

FIG. 7 is a diagram showing dose information stored in the storing device 61 in the embodiment according to the invention.

DETAILED DESCRIPTION OF THE INVENTION

An embodiment of the present invention will be described.

Figure 1:
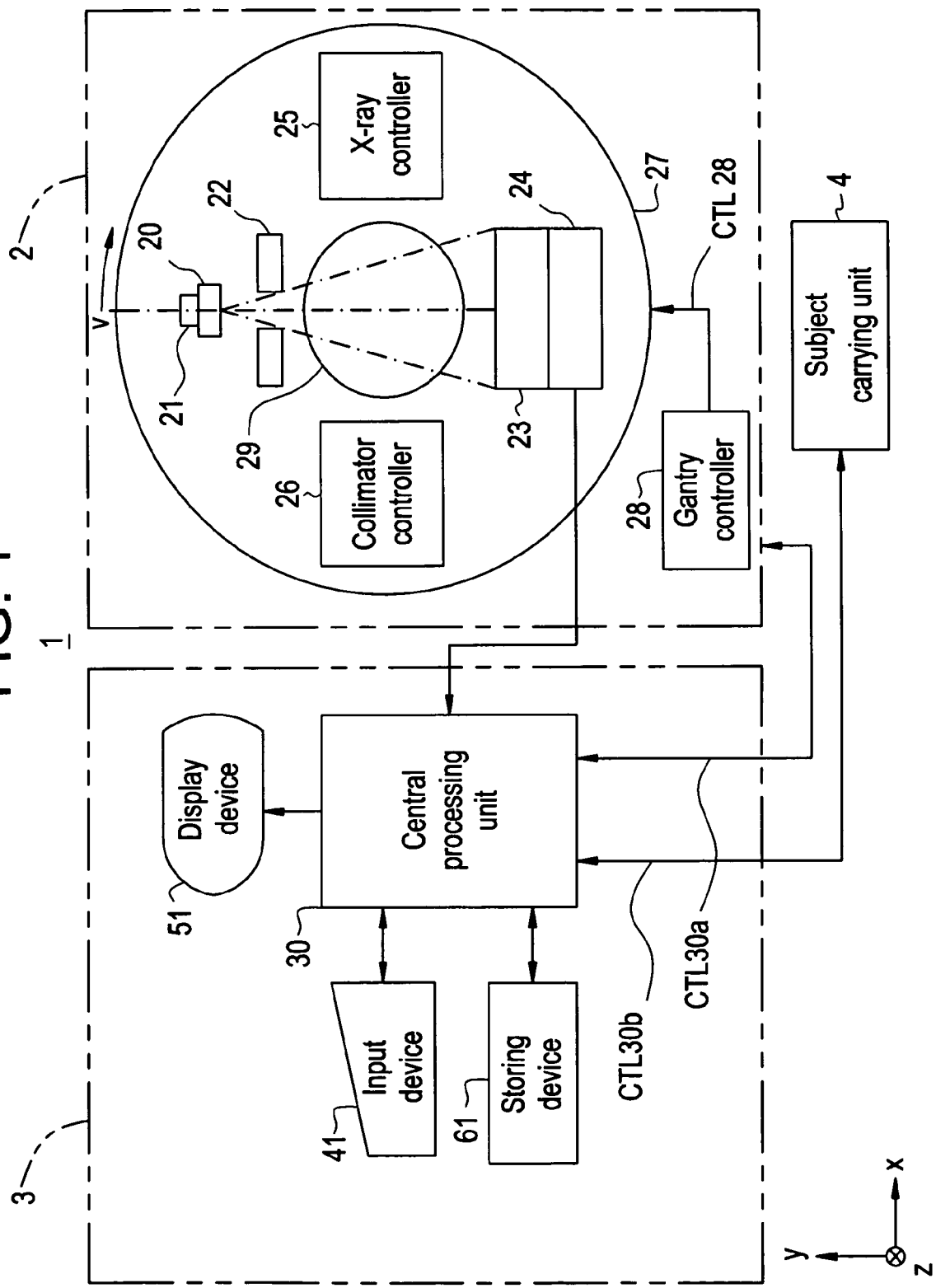
FIG. 1 is a block diagram showing a general configuration of an X-ray CT apparatus in an embodiment according to the invention.
Figure 2:
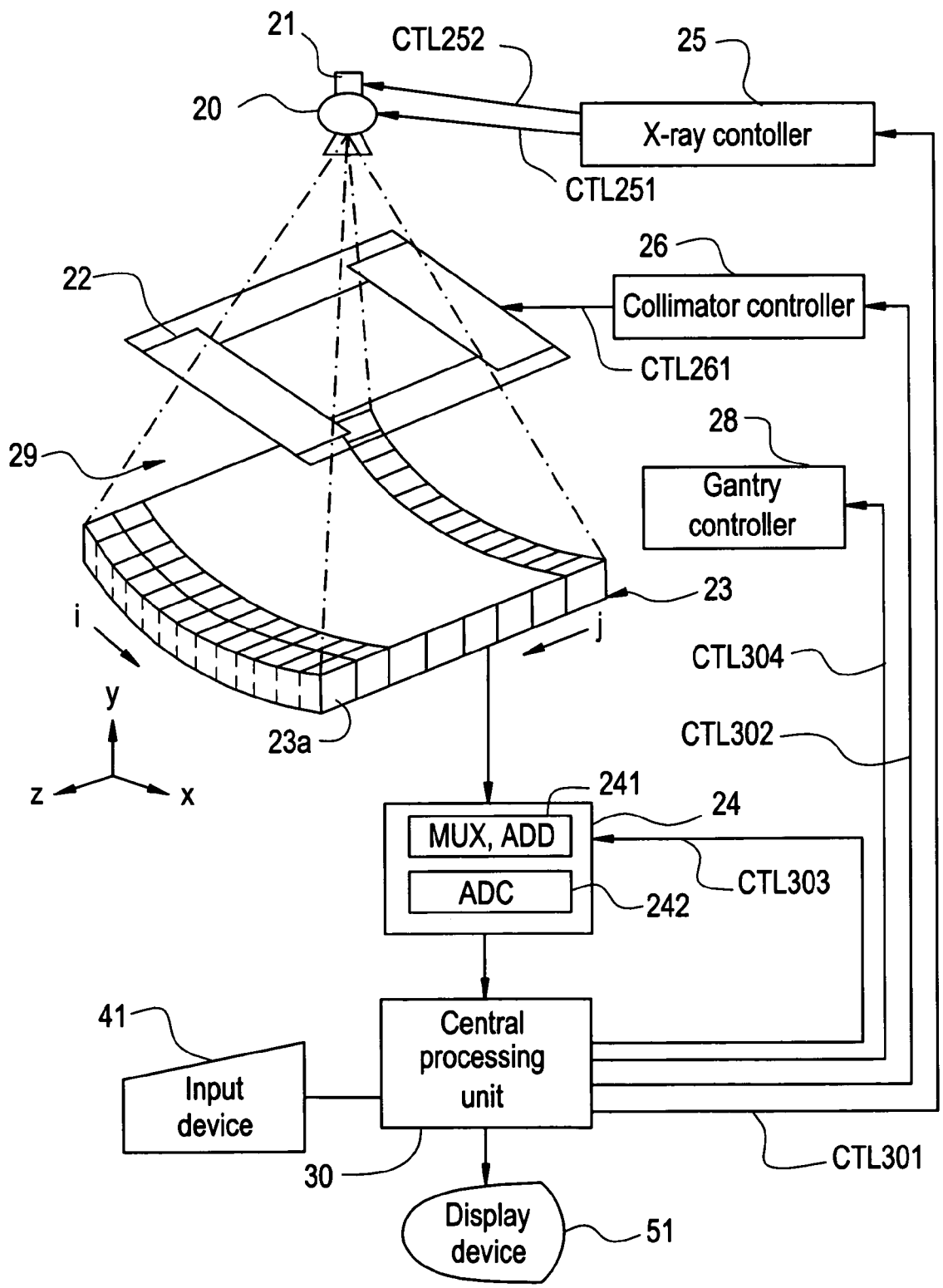
FIG. 2 is a configuration diagram showing a main part of the X-ray CT apparatus in the embodiment according to the invention.

FIG. 1 is a block diagram showing a general configuration of an X-ray CT apparatus 1 of the embodiment according to the invention, and FIG. 2 is a configuration diagram showing a main part in the X-ray CT apparatus 1 of the embodiment.

As shown in FIG. 1, the X-ray CT apparatus 1 has a scan gantry 2, an operation console 3, and a subject carrying unit 4 and reconstructs and generates an image of a section of the subject by using projection data of the subject obtained by scanning the subject with an X-ray on the basis of scan parameters.

The scan gantry 2 will be described.

The scan gantry 2 obtains projection data of the subject by scanning the subject with X-rays, who is moved in a photographing space 29 by the subject carrying unit 4 on the basis of a control signal CTL30a from the operation console 3. As shown in FIG. 1, the scan gantry 2 has an X-ray tube 20, an X-ray tube moving unit 21, a collimator 22, an X-ray detector 23, a data collecting unit 24, an X-ray controller 25, a collimator controller 26, a rotating unit 27, and a gantry controller 28. In the scan gantry 2, as shown in FIG. 2, the X-ray tube 20 and the X-ray detector 23 are disposed so as to sandwich the photographing space 29 in which the subject is carried. The collimator 22 is disposed so as to form an X-ray applied from the X-ray tube 20 to the subject in the photographing space 29. In the scan gantry 2, the X-ray tube 20, the collimator 22, and the X-ray detector 23 are rotated around the subject about a direction "z" of the body axis of the subject as a center. The X-ray tube 20 emits X-rays from a plurality of view directions around the subject, the X-rays from the X-ray tube 20 and passed through the subject are detected by the X-ray detector 23, and projection data is generated. The components of the scan gantry 2 will be described one by one.

The X-ray tube 20 is, for example, a rotating anode X-ray tube and emits X-rays to the subject. As shown in FIG. 2, the X-ray tube 20 emits an X-ray of predetermined intensity to a photographing region in the subject on the basis of a control signal CTL251 from the X-ray controller 25. The X-rays applied from the X-ray tube 20 are formed in, for example, a cone shape by the collimator 22 and emitted to the X-ray detector 23. The X-ray tube 20 rotates around the subject by the rotating unit 27 around the body axis direction "z" of the subject to emit the X-rays to the subject from the view directions around the subject. That is, the X-ray tube 20 rotates around the subject about the axis along the direction in which the subject carrying unit 4 moves the subject in the photographing space 29.

As shown in FIG. 2, the X-ray tube moving unit 21 moves the radiation center of the X-ray tube 20 in the body axis direction "z" of the subject in the photographing space 29 in the scan gantry 2 on the basis of a control signal CTL252 from the X-ray controller 25.

The collimator 22 is disposed between the X-ray tube 20 and the X-ray detector 23 as shown in FIG. 2. The collimator 22 includes, for example, shield plates which do not transmit an X-ray. Two shield plates are provided in the channel direction "i" and two shield plates are provided in the column direction "j". The collimator 22 moves the two shield plates in each of the directions on the basis of a control signal CTL261 from the collimator controller 26 to shield the X-rays applied from the X-ray tube 20 in each of the directions and form the X-rays in a cone shape, thereby adjusting an X-ray irradiation range. That is, the collimator 22 adjusts the X-ray irradiation range by varying the size of the aperture through which an X-ray applied from the X-ray tube 20 passes.

The X-ray detector 23 detects the X-rays applied from the X-ray tube 20 and passed through the subject, and generates projection data of the subject. The X-ray detector 23 is rotated together with the X-ray tube 20 around the subject by the rotating unit 27. The X-ray detector 23 detects the X-rays applied by the X-ray tube 20 around the subject and passed through the subject and generates projection data.

As shown in FIG. 2, the X-ray detector 23 is constructed by a plurality of detection elements 23a. In the X-ray detector 23, for example, the detection elements 23a are disposed two-dimensionally in an array in the channel direction "i" along the rotation direction in which the X-ray tube 20 is rotated by the rotating unit 27 around the subject in the photographing space 29 and the column direction "j" along the rotation axis direction as a center axis of rotating the X-ray tube 20 by the rotating unit 27. For example, in the X-ray detector 23, about 1,000 detection elements 23a are disposed in the channel direction "i", and about 32 to 64 detection elements 23a are disposed in the column direction "j". In the X-ray detector 23, a cylindrical curved concave surface is formed by the plurality of detection elements 23a arranged two-dimensionally.

As the detection elements 23a constructing the X-ray detector 23, for example, a solid-state detector is employed including a scintillator (not shown) for converting an X-ray to light and a photodiode (not shown) for converting the light converted by the scintillator to a charge. The detection element 23a is not limited to a solid-state detector but may be a semiconductor detection element using cadmium tellurium (CdTe) or the like or an ion chamber type detection element using xenon (Xe) gas.

The data collecting unit 24 is provided to collect projection data from the X-ray detector 23. The data collecting unit 24 collects the projection data of the X-rays detected by the detection elements 23a of the X-ray detector 23 and outputs it to the operation console 3. As shown in FIG. 2, the data collecting unit 24 has a selection/addition switching circuit (MUX, ADD) 241 and an analog-digital converter (ADC) 242. The selection/addition switching circuit 241 selects the projection data obtained by the detection elements 23a in the X-ray detector 23 in accordance with a control signal CTL303 from a central processing unit 30, or adds the projection data while changing the combination, and outputs the result to the analog-digital converter 242. The analog-digital converter 242 converts the projection data obtained by selecting the projection data or adding the projection data in an arbitrary combination to a digital signal, and outputs the digital signal to the central processing unit 30.

As shown in FIG. 2, the X-ray controller 25 outputs the control signal CTL251 to the X-ray tube 20 and controls irradiation of the X-rays in accordance with a control signal CTL301 from the central processing unit 30. The X-ray controller 25 controls, for example, tube current in the X-ray tube 20, irradiation time, and the like. The X-ray controller 25 outputs the control signal CTL252 to the X-ray tube moving unit 221 in accordance with the control signal CTL301 from the central processing unit 30 and controls to move the radiation center of the X-ray tube 20 in the body axis direction "z".

As shown in FIG. 2, the collimator controller 26 outputs the control signal CTL261 to the collimator 22 in accordance with a control signal CTL302 from the central processing unit 30 to control the collimator 22 so as to form the X-rays applied from the X-ray tube 20 toward the subject.

As shown in FIG. 1, the rotating unit 27 has a cylindrical shape and the photographing space 29 is formed in the center portion. The rotating unit 27 drives, for example, a motor (not shown) in accordance with a control signal CTL28 from the gantry controller 28 to rotate around the body axis direction "z" of the subject in the photographing space 29 as a center. In the rotating unit 27, the X-ray tube 20, X-ray tube moving unit 21, collimator 22, X-ray detector 23, data collecting unit 24, X-ray controller 25, and collimator controller 26 are mounted. The components are supported by the rotating unit 27. The rotating unit 27 supplies power to the components via a slip ring (not shown). The rotating unit 27 makes the components rotate around the subject to change the relative positional relations between the subject carried in the photographing space 29 and the components in the rotating direction. In the case of performing a scout scan on the subject, the rotating unit 27 rotates and moves the X-ray tube 20 and the X-ray detector 23 to the rotation movement position corresponding to the predetermined view angle around the subject enclosed in the photographing space 29 on the basis of the scout scan parameters set by a scout scan parameter setting unit 304. In the rotation movement position, the rotating unit 27 makes the X-ray tube 20 emit X-rays and makes the X-ray detector 23 detect the X-rays which passed through the subject. In the case of performing the scan on the subject by the axial scanning method, on the basis of the scan parameters set by the a scan parameter setting unit 303, the rotating unit 27 makes the X-ray tube 20 emit X-rays and makes the X-ray detector 23 detect the X-rays passed through the subject at each of a plurality of view angles around the subject while rotating the X-ray tube 20 and the X-ray detector 23 around the subject enclosed in the photographing space 29.

As shown in FIGS. 1 and 2, on the basis of a control signal CTL304 from the central processing unit 30 in the operation console 3, the gantry controller 28 outputs the control signal CTL28 to the rotating unit 27 to execute a control so that the rotating unit 27 rotates.

The operation console 3 will be described.

As shown FIG. 1, the operation control 3 has the central processing unit 30, an input device 41, a display device 51, and a storing device 61. The components will be described one by one.

The central processing unit 30 in the operation console 3 executes various processes on the basis of an instruction entered to the input device 41 by the operator. The central processing unit 30 includes a computer and a program for making the computer function as various means.

Figure 3:
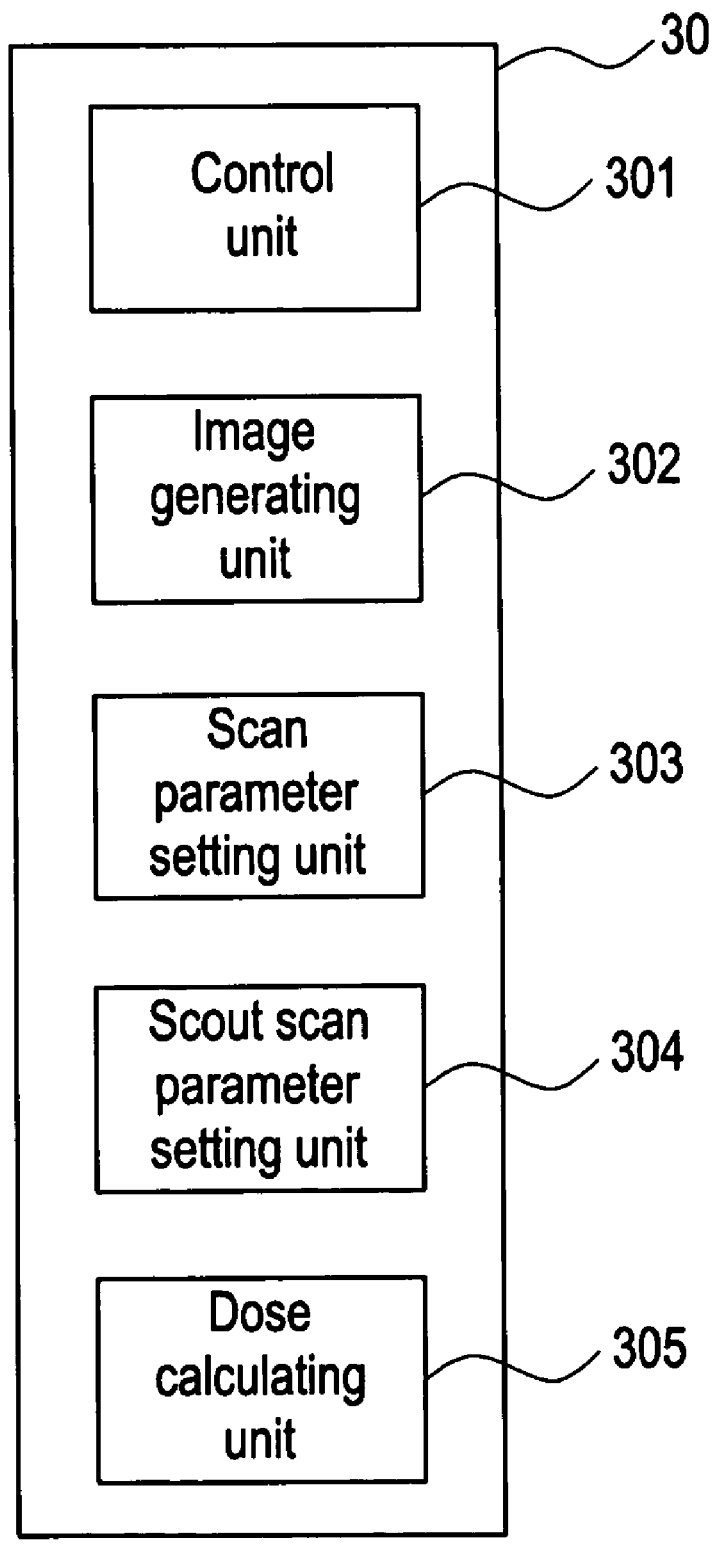
FIG. 3 is a block diagram showing the configuration of a central processing unit in the embodiment according to the invention.

FIG. 3 is a block diagram showing the configuration of the central processing unit 30.

The central processing unit 30 has, as shown in FIG. 3, a control unit 301, an image generating unit 302, the scan parameter setting unit 303, the scout scan parameter setting unit 304, and a dose calculating unit 305. Each of the units has a program for making the computer function various means.

The control unit 301 is provided to control the components in the X-ray CT apparatus 1. The control unit 301 controls the components on the basis of an instruction entered to the input device 41 by the operator. For example, the control unit 301 controls the components so as to be adapted to the scan parameters set by the scan parameter setting unit 303 and executes a scan. The control unit 301 also controls the components so as to be adapted to the scout scan parameters set by the scout scan parameter setting unit 304 and executes a scout scan. Concretely, the control unit 301 outputs a control signal CTL30b to the subject carrying unit 4 to make the subject carrying unit 4 carry and move the subject to the photographing space 29. The control unit 301 outputs the control signal CTL304 to the gantry controller 28 to rotate the rotating unit 27 in the scan gantry 2. The control unit 301 outputs the control signal CTL301 to the X-ray controller 35 so that X-rays are applied from the X-ray tube 20. The control unit 301 outputs the control signal CTL302 to the collimator controller 26 and controls the collimator 22 to form the X-rays. The control unit 301 outputs the control signal CTL303 to the data collecting unit 24 and controls so as to collect projection data obtained by the detection elements 23a in the X-ray detector 23.

The image generating unit 302 generates an image of the subject on the basis of the projection data collected by the data collecting unit 24. In the embodiment, the image generating unit 302 generates a scout image as a radioscopic image of the subject on the basis of the projection data obtained by the scout scan. The image generating unit 302 generates a slice image of a section of the subject on the basis of the projection data obtained by the scan. In the embodiment, a slice image is generated by reconstructing an image of a section of the subject from the projection data obtained by the scan by an image reconstructing method such as a filter process back projecting method.

The scan parameter setting unit 303 sets the scan parameters for operating the components in execution of a scan. For example, the scan parameter setting unit 303 sets the scan method such as the axial scan method or the helical scan method and the scan parameters such as a tube current value for operating the X-ray tube 20 on the basis of the instruction entered to the input device 41 by the operator. The scan parameter setting unit 303 outputs data of the set scan parameters to the control unit 301 to make the control unit 303 control the components.

The scout scan parameter setting unit 304 sets scout scan parameters for operating the components in an execution of a scout scan. The scout scan parameter setting unit 304 sets the scout scan parameters on the basis of the instruction entered to the input device 41 by the operator.

In the embodiment, the scout scan parameter setting unit 304 sets the rotation movement position in which the X-ray tube 20 and the X-ray detector 23 are rotated around the subject and a scout scan is performed on the basis of subject information entered to the input device 41 by the operator. As will be described later, the rotation movement position in which a scout scan is executed is associated with the subject information, and the scout scan parameter setting unit 304 sets a rotation movement position in which a scout scan is performed from the subject information entered to the input device 41 by using the rotation movement information stored in the storing device 61. Concretely, first, the scout scan parameter setting unit 304 receives data of the subject information such as a region, sex, age, body posture, and the like of a subject from the input device 41. After that, the scout scan parameter setting unit 304 extracts data of the rotation movement position corresponding to the subject information from the input device 41 from the rotation movement information stored in the form of a lookup table in the storing device 61. The scout scan parameter setting unit 304 sets the extracted rotation movement position as a scout scan parameter.

The dose calculating unit 305 calculates a dose of the X-rays applied from the X-ray tube 20 to the subject in execution of the scout scan.

In the embodiment, the dose calculating unit 305 obtains, as a reference value, a dose of X-rays applied to the subject in execution of a scout scan on the basis of the subject information entered to the input device 41, the rotation movement position set by the scout scan parameter setting unit 304, and the dose information stored in the storing device 61 which will be described later. In the embodiment, as will be described later, the dose calculating unit 305 calculates the dose of X-rays applied to the subject from the X-ray tube 20 from the subject information and the rotation movement position by using dose information which is stored in the storing device 61 in association with the subject information and the rotation movement position. Concretely, first, the dose calculating unit 305 receives data of the subject information such as a region, sex, age, body posture, and the like of a subject from the input device 41, and also receives data of the rotation movement position in which a scout scan is executed from the scout scan parameter setting unit 304. After that, the dose calculating unit 305 calculates data of the dose corresponding to the subject information and the rotation movement position from the dose information stored in the form of a lookup table in the storing device 61.

The input device 41 in the operation console 3 is constructed by, for example, a keyboard, a mouse, and the like. The input device 41 enters various information such as scan parameters and subject information and instructions to the central processing unit 30 on the basis of an input operation of the operator. For example, at the time of performing a scout scan, the input device 41 enters, as the subject information, a region in the subject, sex of the subject, age of the subject, and the posture of the subject supported by a table 401 in the subject carrying unit 4.

The display device 51 in the operation console 3 includes, for example, a CRT and displays an image on a display screen on the basis of an instruction from the central processing unit 30.

In the embodiment, the display device 51 displays the scout image generated by the image generating unit 302 on the display screen by execution of the scout scan. The display device 51 displays the value of the dose calculated by the dose calculating unit 305 onto the display screen. In addition, the display device 51 displays the slice image generated by the image generating unit 302 by execution of the scan onto the display screen.

The storing device 61 in the operation console 3 is a memory and stores various data. The stored data in the storing device 61 is accessed by the central processing unit 30 as necessary.

In the embodiment, the storing device 61 stores, as rotation movement information, the rotation movement position in which a scout scan is executed in association with the subject information. The storing device 61 stores, in the form of a lookup table, the rotation movement information of the rotation movement position associated with the subject information such as a region, sex, age, and body posture of the subject. As described above, when the scout scan parameter setting unit 304 receives data of the subject information such as a region, sex, age, and body posture of the subject from the input device 41, the storing device 61 is accessed by the scan parameter setting unit 304, and the data of the rotation movement position associated with the subject information from the input device 41 is extracted from the rotation movement information stored in the form of the lookup table. The extracted rotation movement position is set as a scout scan parameter by the scout scan parameter setting unit 304.

In the embodiment, the storing device 61 stores, as dose information, the dose of X-rays applied from the X-ray tube 20 to the subject in a scout scan in association with the subject information and the rotation movement position. The storing device 61 stores, in the form of a lookup table, the dose information of the dose associated with the subject information such as a region, sex, age, and body posture of the subject and the rotation movement position in which the rotating unit 27 rotates and moves the X-ray tube 20 and the X-ray detector 23 at the time of execution of a scout scan. As described above, when the dose calculating unit 305 receives the data of the subject information such as a region, sex, age, and body posture of the subject from the input device 41 and receives the data of the rotation movement position in which a scout scan is performed from the scout scan parameter setting unit 304, the storing device 61 is accessed by the dose calculating unit 305, and the data of the dose associated with the subject information and the rotation movement position is extracted.

The subject carrying unit 4 will be described.

The subject carrying unit 4 carries a subject between the inside and the outside of the photographing space 29.

Figure 4:
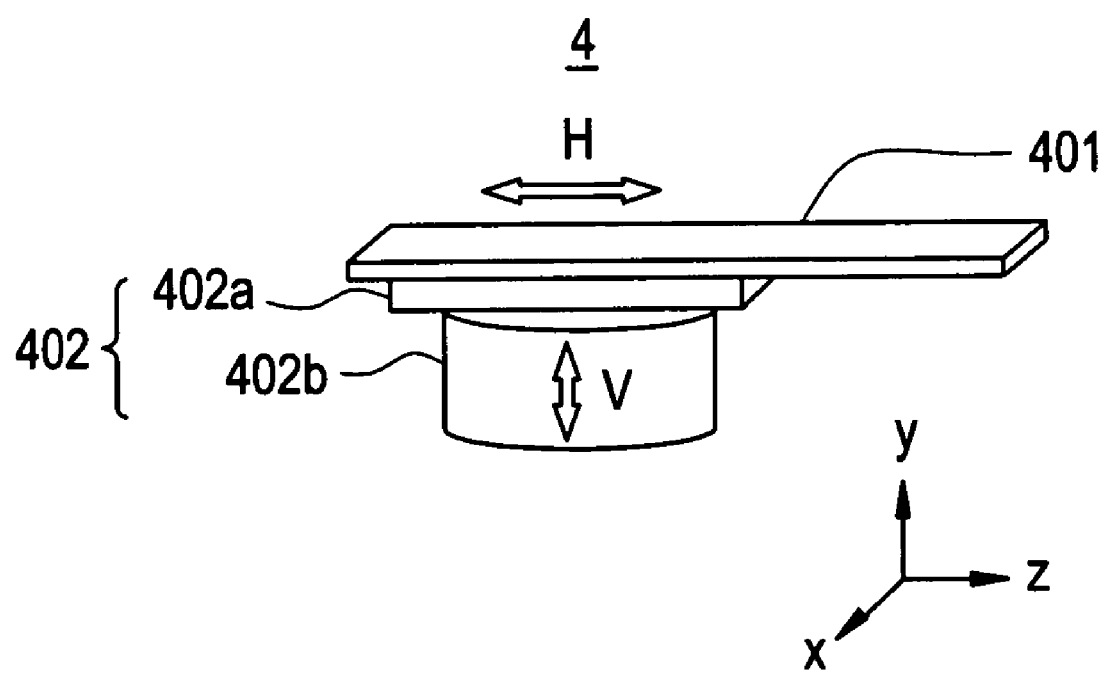
FIG. 4 is a perspective view showing the configuration of a subject carrying unit in the embodiment according to the invention.

FIG. 4 is a perspective view showing the configuration of the subject carrying unit 4.

As shown in FIG. 4, the subject carrying unit 4 has the table 401 and a table moving unit 402.

In the table 401 in the subject carrying unit 4, a mounting surface on which the subject is mounted is formed, and a subject is supported by the mounting surface. For example, the subject is placed on his or her back on the table and is supported by the table 401 in the subject carrying unit 4.

The table moving unit 402 in the subject carrying unit 4 has a horizontal-direction moving unit 402a for moving the table 401 in a horizontal direction H along the body axis direction "z" of the subject and a perpendicular-direction moving unit 402b for moving the table 401 in a vertical direction V perpendicular to the horizontal direction H, and moves the table 401 so as to carry the subject into the photographing space 29 on the basis of the control signal CTL30b from the central processing unit 30.

The operations of the X-ray CT apparatus 1 of the embodiment will be described.

Figure 5:
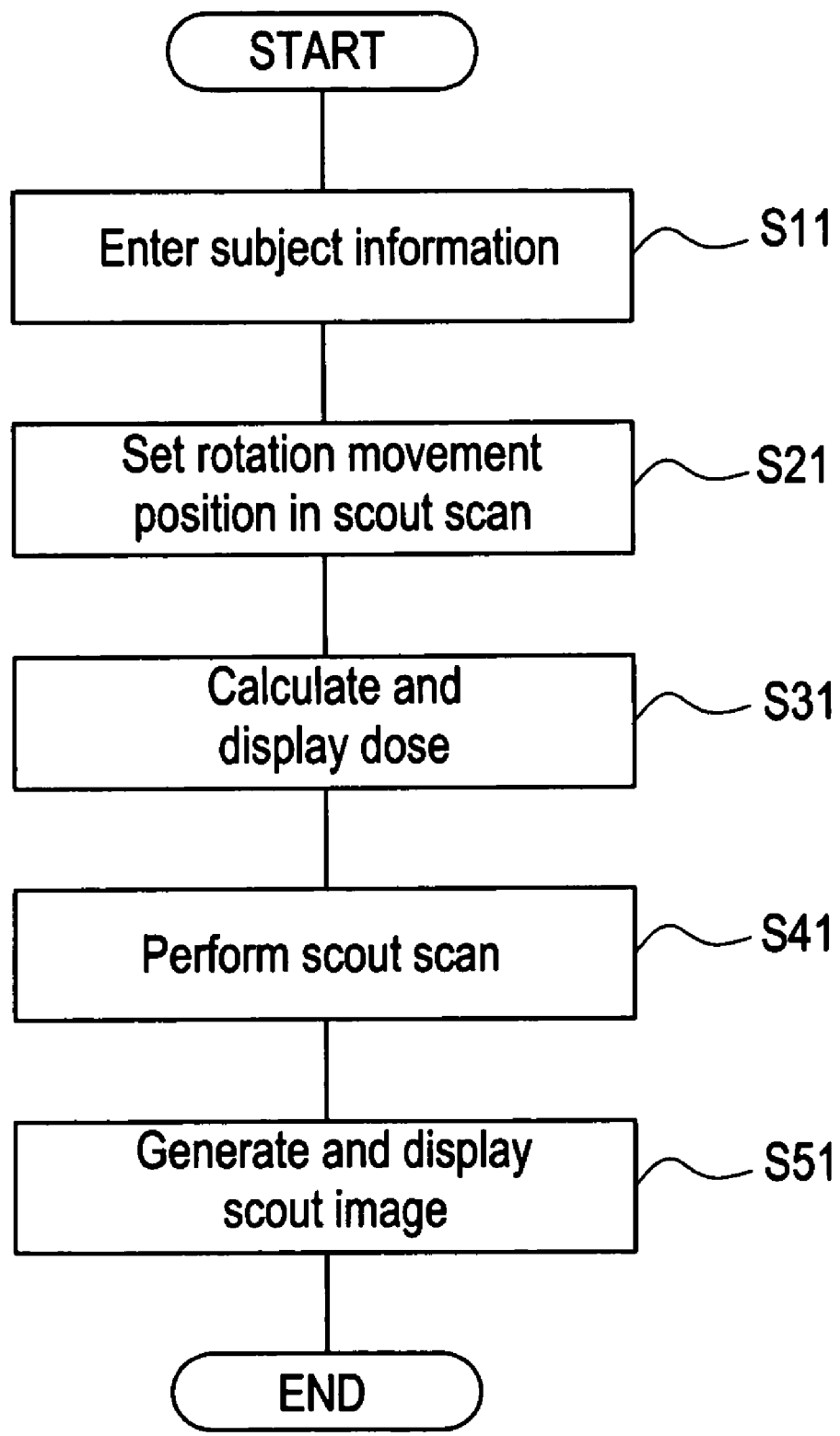
FIG. 5 is a flowchart showing main operations at the time of performing a scout scan on a subject in the embodiment according to the invention.

FIG. 5 is a flowchart showing main operations performed at the time of performing a scout scan on a subject.

As shown in FIG. 5, first, the subject information is entered (S11).

In execution of a scout scan, the input device 41 in the operation console 3 enters, as subject information, a region in the subject corresponding to the slice position in which a scout image is generated, sex of the subject, age of the subject, and the body posture of the subject supported by the table 401 of the subject carrying unit 4 on the basis of the input operation of the operator. For example, data "chest region" is entered as the region in the subject, data "female" is entered as sex of the subject, data "20" is entered as age of the subject, and data "face-up position" is entered as the body posture of the subject.

Next, as shown in FIG. 5, the rotation movement position in a scout scan is set (S21).

The scout scan parameter setting unit 304 sets the rotation movement position in which the rotating unit 27 rotates the X-ray tube 20 and the X-ray detector 23 around the subject at the time of executing a scout scan on the basis of the subject information entered as described above. Concretely, the scout scan parameter setting unit 304 receives the data of the subject information such as region, sex, age, and body posture of the subject from the input device 41. After that, the scout scan parameter setting unit 304 extracts the data of the rotation movement position corresponding to the subject information received from the input device 41 from the rotation movement information stored in the form of a lookup table in the storing device 61.

FIG. 6 is a diagram showing the rotation movement information stored in the storing device 61.

As shown in FIG. 6, the storing device 61 stores a view angle "v" as the rotation movement position so as to be associated with the subject information of region, sex, age, and body posture of the subject. The view angle "v" denotes an angle through which the X-ray tube 20 is moved so as to rotate around the subject from the vertical direction "y" which is set as 0° as shown in FIG. 1.

In the embodiment, in the case where the scout scan parameter setting unit 304 receives, as the subject information, the data indicating that, as described above, for example, the region in the subject is a chest region, sex of the subject is female, age of the subject is 20, and body posture of the subject is face-up position, the scout scan parameter setting unit 304 extracts the view angle of 180° as the rotation movement position from the rotation movement information as shown in FIG. 6. The scout scan parameter setting unit 304 sets the extracted rotation movement position as a scout scan parameter. The scout scan parameter setting unit 304 also sets the other scout scan parameters on the basis of an instruction entered to the input device 41 by the operator.

Next, as shown in FIG. 5, a dose is calculated and displayed (S31).

In execution of a scout scan, the dose calculating unit 305 calculates a dose of X-rays applied from the X-ray tube 20 to the subject. In the embodiment, by using the dose information stored in the storing device 61, the dose calculating unit 305 calculates the dose of exposure of the subject during execution of the scout scan on the basis of the subject information entered by the input device 41 and the rotation movement position set by the scout scan parameter setting unit 304.

Concretely, first, the dose calculating unit 305 receives the data of the subject information such as region, sex, age, and body posture of the subject and the data of the rotation movement position in which the scout scan is executed from the input device 41 and the scout scan parameter setting unit 304, respectively. After that, the dose calculating unit 305 obtains data of the dose corresponding to the subject information and the rotation movement position from the dose information stored in the form of the lookup table in the storing device 61.

FIG. 7 is a diagram showing dose information stored in the storing device 61.

As shown in FIG. 7, the storing device 61 stores, as dose information, a dose of X-rays applied from the X-ray tube 20 to the subject in a scout scan in association with the subject information such as region, sex, age, and body posture of the subject and the rotation movement position. The exposure information is preliminarily obtained by, for example, executing a scan on a human phantom with predetermined scan parameters, and stored in the storing device 61. Consequently, as described above, in the case where, for example, the scout scan parameter setting unit 304 receives data indicating that the region in the subject is a chest region, sex of the subject is female, and the body posture of the subject is a face-up position, and sets the view angle of 180° as the rotation movement position, the dose calculating unit 305 calculates, as a dose, 1.2 mGy as an organ dose for the mammary gland on the basis of the dose information as shown in FIG. 7. After that, the display device 51 receives the data of the dose calculated by the dose calculating unit 305 and displays it on the display screen.

Next, as shown in FIG. 5, a scout scan is executed (S41).

The control unit 301 controls the components on the basis of the scout scan parameters set by the scout scan parameter setting unit 304, thereby performing a scout scan.

Figure 8:
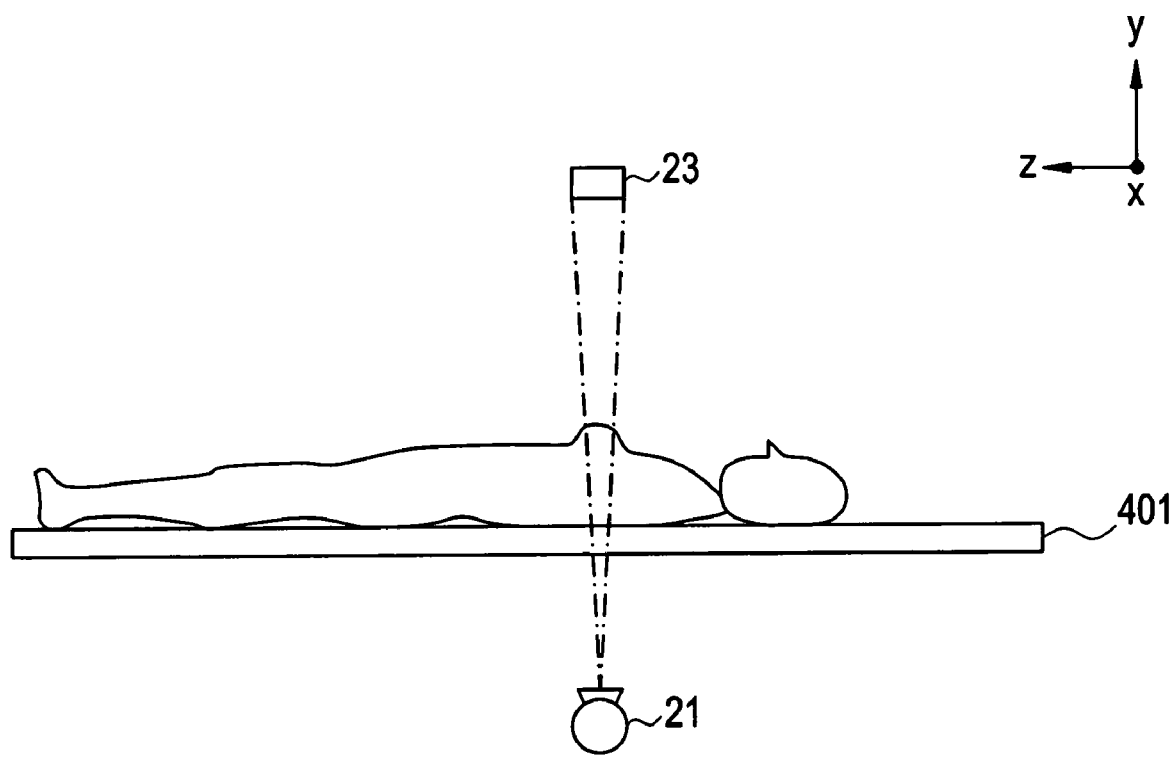
FIG. 8 is a side view showing a state where a scout scan is performed in the embodiment according to the invention.

FIG. 8 is a side view showing a state where a scout scan is performed.

As shown in FIG. 8, in the embodiment, the control unit 301 controls the rotation movement operation of the rotating unit 27 so as to be adapted to the view angle of 180° which is set as the rotation movement position by the scout scan parameter setting unit 304. Specifically, the control unit 301 makes the rotating unit 27 adjust the positions of the X-ray tube 20 and the X-ray detector 23 so that the X-ray tube 20 applies X-rays from the back side to the chest region of the female subject placed on the table 401 in the body posture of the face-up position and, on the front side, the X-ray detector 23 detects the X-rays passed through the subject. After that, on the basis of the scout scan parameters set by the scout scan parameter setting unit 304, X-rays are applied from the X-ray tube 20 to the subject at the view angle 180° set as the rotation movement position, and the X-rays passed through the subject are detected by the X-ray detector 23, thereby performing a scout scan.

Next, as shown in FIG. 5, a scout image of the subject is generated and displayed (S51).

In this case, the image generating unit 302 generates a scout image as a radioscopic image of the subject on the basis of projection data obtained by execution of the scout scan. The display device 51 displays the scout image generated by the image generating unit 302 by the execution of the scout scan onto the display screen.

As described above, in the embodiment, the scout scan parameter setting unit 304 sets the rotation movement position in which the X-ray tube 20 and the X-ray detector 23 are moved so as to rotate around the subject at the time of executing a scout scan on the basis of the subject information of the subject on which the scout scan is performed. Upon start of execution of the scout scan, the rotating unit 27 rotates and moves the X-ray tube 20 and the X-ray detector 23 around the subject to the rotation movement position set by the scout scan parameter setting unit 304. After that, a scout scan is executed in the rotation movement position. For example, in the case of performing a scout scan on the chest region of the female subject placed on the table 401 in the body posture of the face-up position, the rotating unit 27 adjusts the positions of the X-ray tube 20 and the X-ray detector 23 so that the X-ray tube 20 applies X-rays from the back side of the subject and the X-ray detector 23 detects the X-rays passed through the subject on the front side. With the configuration, the dose on the mammary gland of the subject is reduced to ⅕ to ⅙ of the dose in the case of applying X-rays from the front side. In the embodiment, also in the case of performing a scout scan on a chest region of a female subject so as to include the mammary gland having high radiation sensitivity, by applying X-rays from the back side of the subject, the dose can be reduced. An image can be acquired by efficiently utilizing X-rays.

In the foregoing embodiment, the X-ray CT apparatus 1 corresponds to a radiographic apparatus of the invention. In the embodiment, the X-ray tube 20 corresponds to an irradiator of the present invention. In the embodiment, the X-ray detector 23 corresponds to a detector of the invention. In the embodiment, the rotating unit 27 corresponds to a rotating unit of the invention. In the embodiment, the input device 41 corresponds to an input unit of the invention. In the embodiment, the display device 51 corresponds to a display unit of the invention. In the embodiment, the storing device 61 corresponds to a first storing unit, a second storing unit, a third storing unit, a fourth storing unit, and a fifth storing unit of the invention. In the embodiment, the scout scan parameter setting unit 304 corresponds to a setting unit of the invention. In the embodiment, the dose calculating unit 305 corresponds to a dose calculating unit of the invention. In the embodiment, the table 401 corresponds to a table of the invention.

At the time of carrying out the present invention, the invention is not limited to the foregoing embodiment but various modifications can be employed.

For example, an example of using X-rays as radiation rays has been described in the foregoing embodiment, but the invention is not limited to the example. For example, radiation rays such as gamma rays may be also employed.

In addition, at the time of setting the rotation movement position in which a scout scan is performed, the scout scan setting unit 304 may calculate the distance between a region in a subject entered by the input device 41 and the X-ray tube 20 and sets the rotation movement position to which the X-ray tube 20 is rotated and moved by the rotating unit 27 so that the distance between the region in the subject and the X-ray tube 20 is shortened. For example, at the time of performing a scout scan on the chest region in a female subject placed on the table 401 in the face-up body posture, the distance between the mammary gland having high sensitivity in the chest region in the subject and the X-ray tube 20 is calculated in various positions to which the X-ray tube 20 is moved so as to rotate around the subject. For example, coordinate position information of a region in the subject is stored in the storing device 61 and the distance between the region in the subject and the X-ray tube 20 is calculated by using the coordinate position information. The rotation movement position of the X-ray tube 20 corresponding to the back of the subject in which the distance between the mammary gland in the chest region in the subject and the X-ray tube 20 is the shortest is set as the rotation movement position to which the X-ray tube 20 is rotated and moved at the time of a scout scan. The scout scan setting unit 304 may also select a rotation movement position corresponding to the smallest dose from data of a plurality of doses corresponding to the subject information entered by the input device 41 in the dose information stored in the storing device 61 and set the selected position.

The invention claimed is:

1. A radiographic apparatus for generating a scout image of a subject, said apparatus comprising:
   an irradiator for irradiating the subject with radiation rays;
   a detector for detecting the radiation rays applied by said irradiator and passed through the subject;
   a rotating unit for moving said irradiator and said detector so as to rotate around the subject to a position for performing a scout scan;
   an input unit for inputting subject information for the subject on which the scout scan is performed;
   a storing unit for storing said position in association with the subject information, said position of said irradiator selected from two irradiator positions that vary by a 180 degree view angle inputted into said input unit, a first irradiator position of the two irradiator positions providing a reduced dose of radiation rays on a region of the subject compared to a second irradiator position of the two irradiator positions, said irradiator applying radiation rays to the subject only in said position; and
   a setting unit for setting said position of said irradiator in which the scout scan is performed by reading said position of said irradiator from said storing unit in association with the subject information inputted into said input unit.

2. A radiographic apparatus according to claim 1 wherein:
   the subject information includes a region of the subject;
   said storing unit stores said position of said irradiator for performing the scout scan in association with the region of the subject; and
   said setting unit sets said position of said irradiator by reading said position of said irradiator from said storing unit in association with the region of the subject inputted into said input unit.

3. A radiographic apparatus according to claim 1 wherein:
   the subject information includes a sex of the subject;
   said storing unit stores said position of said irradiator for performing the scout scan in association with the sex of the subject; and
   said setting unit sets said position of said irradiator by reading said position of said irradiator from said storing unit in association with the sex of the subject inputted into said input unit.

4. A radiographic apparatus according to claim 1 wherein:
   the subject information includes an age of the subject;
   said storing unit stores said position of said irradiator for performing the scout scan in association with the age of the subject; and
   said setting unit sets said position of said irradiator by reading said position of said irradiator from said storing unit in association with the age of the subject inputted into said input unit.

5. A radiographic apparatus according to claim 1 further comprising:
   a table having a mounting surface on which the subject is mounted and supported, wherein:
   the subject information includes a body posture of the subject;
   said storing unit stores said position of said irradiator for performing the scout scan in association with the body posture of the subject inputted into said input unit; and
   said setting unit sets said position of said irradiator by reading said position of said irradiator from said storing unit in association with the body posture of the subject inputted into said input unit.

6. A radiographic apparatus according to claim 1 wherein said storing unit stores, as dose information, a dose of radiation rays applied to the subject by the irradiator, in association with the subject information and said position of said irradiator, said radiographic apparatus further comprising a dose calculating unit that calculates the dose of radiation rays applied to the subject by said irradiator on the basis of the subject information inputted into said input unit and the dose information stored in said storing unit.

7. A radiographic apparatus according to claim 6 further comprising a display unit for displaying the dose calculated by said dose calculating unit.

8. A radiographic apparatus according to claim 1 wherein the radiation rays are X-rays.

9. A method for performing a scout scan, said method comprising:
   inputting subject information for a subject on which the scout scan is performed;
   setting a position of an irradiator in association with the inputted subject information, the position of the irradiator selected from two irradiator positions that vary by a 180 degree view angle, a first irradiator position of the two irradiator positions providing a reduced dose of radiation rays on a region of the subject compared to a second irradiator position of the two irradiator positions, said irradiator applying radiation rays to the subject only in said position; and
   performing the scout scan of the subject in the position of the irradiator.

10. A method according to claim 9 wherein inputting the subject information further comprises inputting subject information including the region of the subject.

11. A method according to claim 9 wherein inputting the subject information further comprises inputting subject information including a sex of the subject.

12. A method according to claim 9 wherein inputting the subject information further comprises inputting subject information including an age of the subject.

13. A method according to claim 9 wherein inputting the subject information further comprises inputting subject information including a body posture of the subject on a scanning table.

14. A method for performing a scout scan of a subject using a radiographic apparatus comprising an irradiator, a detector, a rotating unit, an input unit, a storing unit, a setting unit, and a dose unit, said method comprising:
   inputting subject information into the input unit for the subject on which the scout scan is performed;
   storing a position of the irradiator for performing the scout scan associated with the inputted subject information, the position of the irradiator selected from two irradiator positions that vary by a 180 degree view angle, a first irradiator position of the two irradiator positions providing a reduced dose of radiation rays on a region of the subject compared to a second irradiator position of the two irradiator positions;
   setting the position of the irradiator in which the scout scan is performed by reading the position of the irradiator from the storing unit;
   calculating the dose of radiation rays;
   rotating the irradiator and the detector around the subject to the set position of the irradiator;
   irradiating the subject with radiation rays emitted from the irradiator only in said position; and
   detecting the radiation rays applied by the irradiator and passed through the subject.

15. A method according to claim 14 wherein inputting subject information further comprises inputting into the input unit at least one of the region of the subject, a sex of the subject, an age of the subject, and a body posture of the subject.

16. A method according to claim 14 wherein storing the position of the irradiator further comprises storing the position of the irradiator in the storing unit based on at least one of the region of the subject, a sex of the subject, an age of the subject, and a body posture of the subject.

17. A method according to claim 14 wherein setting the position of the irradiator further comprises:

reading the stored position of the irradiator from the storing unit; and setting the position of the irradiator based on the read position of the irradiator.

18. A method according to claim 14 wherein calculating a dose of radiation rays applied to the subject further comprises calculating the dose of radiation rays based on at least one of the region of the subject, a sex of the subject, an age of the subject, and a body posture of the subject, and a dose information stored in the storing unit.

19. A method according to claim 14 wherein irradiating the subject further comprises applying X-rays as the radiation rays.

* * * * *